United States Patent [19]

Alford et al.

[11] 4,376,583

[45] Mar. 15, 1983

[54] SURFACE INSPECTION SCANNING SYSTEM

[75] Inventors: W. Jerry Alford; Charles J. Cushing; James D. Hunt, all of Charlotte; Michael L. Smith, Matthews; Richard D. Vander Neut, Charlotte; James L. Wilkes, Matthews, all of N.C.

[73] Assignee: Aeronca Electronics, Inc., Pineville, N.C.

[21] Appl. No.: 262,866

[22] Filed: May 12, 1981

[51] Int. Cl.³ .......................................... G01N 21/00
[52] U.S. Cl. ................................. 356/237; 250/563; 250/572; 356/431
[58] Field of Search ................... 356/430, 431, 237; 250/562, 563, 572; 209/577, 579, 587

[56] References Cited

U.S. PATENT DOCUMENTS

| | | | |
|---|---|---|---|
| 3,743,431 | 7/1973 | Cushing et al. | 356/239 |
| 3,781,117 | 12/1973 | Laycak et al. | 356/237 X |
| 3,781,531 | 12/1973 | Baker | 235/151.3 |
| 3,790,287 | 2/1974 | Cuthbert et al. | 356/120 |
| 3,859,537 | 1/1975 | Wolf | 250/559 |
| 3,866,054 | 2/1975 | Wolf | 250/562 |
| 3,900,265 | 8/1975 | Merlen et al. | 356/200 |
| 3,958,127 | 5/1976 | Faalhaber et al. | 250/572 X |
| 4,028,506 | 6/1977 | Araseki et al. | 179/170.2 |
| 4,030,830 | 6/1977 | Holly | 356/109 |
| 4,075,498 | 2/1978 | Takasuka et al. | 250/572 X |
| 4,155,012 | 5/1979 | Clarke et al. | 250/563 |
| 4,173,441 | 11/1979 | Wolf | 356/431 |
| 4,197,011 | 4/1980 | Hudson | 356/354 |
| 4,237,539 | 12/1980 | Piovoso et al. | 356/430 X |

OTHER PUBLICATIONS

"A Laser Scan Technique for Electronic Materials Surface Evaluation" by D. R. Oswald & D. F. Munro, *Journal of Electronic Materials;* vol. 3, No. 1, pp. 225-242, 1974.

"Silicon Slice Analyzer Using a He-Ne Laser" by H. J. Ruiz et al., *Journal of Electrochemical Society: Solid State Sci. & Tech.,* May, 1974, pp. 689-692.

Defensive Publication 749337 to Buckson, "Defect Detector Having Rotating Prism Scanner Having Plurality of Pairs of Photocells With Coloring and Space Filtering".

*Primary Examiner*—John K. Corbin
*Assistant Examiner*—Matthew W. Koren
*Attorney, Agent, or Firm*—Paul K. Godwin, Jr.

[57] ABSTRACT

A system for laser scanning a relatively movable reflective surface element and inspecting that surface by monitoring the reflected energy in both light and dark channel receivers. Flaws occurring on the surface of the element, depending on the types of flaws, cause various frequency components to be present in the reflected energy and affect the amount of energy reflected to the light and dark channel receivers. Circuitry is included to detect and classify the various types of flaws as they are scanned, to compute the condition of the inspected element and to grade that inspected element as being in an acceptable state or in one of a plurality of unacceptable states. The described reflective surface element is a silicon wafer of the type used as the base substrate in fabricating integrated circuits and other electronic components.

22 Claims, 9 Drawing Figures

SURFACE INSPECTION SCANNING SYSTEM

BACKGROUND OF THE INVENTION

1. Field of the Invention

The present invention is directed to the field of automatic surface inspection systems and more particularly to the inspection of highly reflective surfaces such as silicon wafers, for minute flaws.

2. Description of the Prior Art

Semiconductor manufacturers utilize silicon wafer discs for the base substrate in the manufacture of solid state electronic components, such as transistors and integrated circuits.

The occurrence of various types of flaws, such as dust, dirt, crystal imperfections, scratches, haze and pits, down to the low micron size are detrimental to the component fabrication process and adversely affect the yield of individual components in production.

At present, a manual, visual inspection technique is used by most manufacturers of the silicon wafers and fabricators of integrated circuits. The manual technique employs an intense light source to illuminate the wafer surface. A human inspector adjusts the wafer to an appropriate angle of light reflection and visually observes the wafer surface for several seconds to determine the surface quality of the wafer. While the manual technique is adequate for detecting dirt and dust particles and scratches down to approximately 5 microns, imperfections of lesser size go undetected.

A description of a technique utilizing a scanning laser beam to inspect silicon wafers is found in an article entitled "A Laser Scan Technique for Electronic Material Surface Evaluation" by D. R. Oswald and D. F. Monroe, published in the *Journal of Electronic Materials*, Vol. 3, No. 1, 1974, pages 225-241. In the described device, a beam of electromagnetic radiation from a three milliwatt laser is first expanded from its original diameter to a larger diameter and is directed unto a torsional oscillating mirror that directs the expanded beam at 90° into a lens. The rotational axis of the mirror lies in the front focal plane of the lens and intersects its optic axis. The wafer surface to be examined is positioned on the other side of the lens, one focal length from it. The focused beam is normally incident to the surface of the wafer and is line-scanned over the surface as the wafer is transversely transported past the scanning line.

In the absence of defects, all the light is said to be normally reflected from the surface and follows the incident path in reverse. When the focused spot strikes the wafer surface and encounters a defect, light is said to be scattered by that defect so that the regional space immediately surrounding the main return beam contains the scattered light energy. An apertured mirror is placed in the beam path between the laser generator and the oscillating mirror so as to allow transmission of the expanded beam from the generator to the oscillating mirror and provide a reflecting surface for the received scattered light.

The scattered light reflected from the apertured mirror is focused by a receiving lens onto a signal detector. The variation in the scattered light received by the signal detector is used to indicate the presence of defects on the surface of the wafer.

A memory oscilliscope and defect counter are employed to show location and accumulate the occurrence of defects, respectively.

The prior art device is described as successfully detecting and counting defects greater than 8 microns in diameter and some defects down to 1 micron in size, providing they have proper light scattering characteristics.

SUMMARY OF THE INVENTION

While prior art attempts to develop automatic inspection systems met with limited success in laboratory and prototype embodiments, the industry has not found such systems to be acceptable over the manual technique described above. The basic needs of the semiconductor industry are for a complete inspection system that can detect minute flaws (1 micron or greater) in silicon wafers, distinguish those flaws by type classification and automatically grade each inspected wafer as acceptable or varying degrees of rejection based upon manufacturer or customer specification of flaw tolerances.

The types of flaws recognized in the industry are defined in the American National Standard Institute, Inc. ASTM F154-76 and are classified as scratches; pits; embedded abrasive grains; haze; contamination; edge chips ; cracks; crows feet; craters; dimples; grooves; mounds; orange peel; saw marks; and striations;

The process of preparing each silicon wafer includes the steps of sawing the wafer disc from the grown boule; polishing the disc; cleaning the disc; and handling. During that process, one or more of the aforementioned flaws may be caused to be present on the prepared wafer disc. In some cases, such as those in which only dust is present, it would not be necessary to reject the wafer entirely, but rather, return it through the cleaning step to remove the dust. On the other hand, if flaws such as pits, haze or scratches were present, those wafers might be brought to an acceptance level by recycling them through both the polishing and cleaning steps. Gross flaws, in a wafer surface, such as saw marks and other severe distortions, may require that wafers be rejected as completely unacceptable.

The present invention provides an automatic system for inspecting wafer surfaces by detecting and classifying flaws, as well as grading each inspected wafer. The system, as described herein, is a laser based automated high speed inspection system capable of resolving an individual imperfection to one micron in size. The types of flaws detected include those defined by ANSI and noted above.

The system consists of an automatic transport handling system, an optical inspection section and a signal processing section incorporating electronic circuitry for analyzing the inspection information and controlling the sorting of individual wafers.

A feed-through transport system provides supply capabilities for the individual wafers from storage cassettes to an inspection zone and from the inspection zone to separately "graded" cassettes, according to the respective inspection results. The transport system contains input elevator modules to automatically unload wafers one at a time, a transport spine to move the wafer through the inspection zone and output elevator modules to automatically sort and load wafers one at a time into appropriately selected cassettes. The graded categories are ACCEPT, RECLEAN, REPOLISH and REJECT.

The optical inspection section includes a low power helium neon laser source that is focused at a plane coincident with the transported wafer surface. The beam is repetitively scanned in a line transverse to the direction of wafer transport to provide 100% inspection. Reflections from the wafer are received by twin fiber optic collectors separately spaced so as to respectively collect the specularly reflected light and scattered light. The specular collector has a narrow slit aperture so that any change in parallelism of the surface causes the specularly reflected beam to move with respect to the slit and decrease the amount of energy transmitted into the collector. The scattered light collector is located approximately normal to the surface of the wafer and collects a portion of the light that is scattered by any diffused particle or surface perturbation.

Light collected by the fiber optic collectors is passed through dichrioic filters to eliminate any ambient light other than that of the laser wavelength. The collected light is then directed to a pair of photo-multiplier tubes to provide electrical output signals to the signal processing section.

The signal processing section includes analog circuitry for receiving electrical output signals from the photo-multiplier tubes and for providing seven channels of real time information in the form of a seven bit address. The information in the seven channels is derived by comparing the electrical output signals with various threshold levels, in the case of the received scattered light; and by extracting various frequency components and comparing those components with predetermined threshold levels, in the case of the received specularly reflected light.

Three of the seven channels correspondingly contain information obtained from the scattered light receiving photo-multiplier output signal by comparing that signal with three separate threshold levels. The remaining four channels correspondingly contain information obtained from the reflected light receiving photo-multiplier output signal, by filtering the signal to pass separate frequency components and then comparing those components with separate threshold levels, in the case of three, and comparing the output signal with the threshold level, in the case of the fourth.

The seven bit address is applied to a flaw handling logic network, which is used to construct a digital surface map of the wafer under inspection. The scan wafer is divided into a large number of minute areas and each unit area is assigned a binary code which represents the most severe flaw type encountered within the unit area. The unit area in which no flaws are detected would be represented by an all zero's code.

The location code and flaw code representation for each unit area is temporarily stored in memory, where it is available as information essential to the grading and sorting of the inspected wafer.

An algorithm for grading each inspected wafer compares the accumulated number of stored flaw codes according to a prioritization routine, as dictated by the user. The number of most severe flaw codes are compared with an acceptable number value and that number is added to the total of a less severe flaw code if that number is within the acceptable number value. The number of next most severe flaw codes are then compared with an acceptable number value for that flaw code and that number is added to the total of a less severe flaw code if that number is within the acceptable number value. This procedure is continued until one of the acceptable number values is exceeded or all the flaw codes are scrutinized and none of the acceptable number of values are found to be exceeded. In the first instance, the wafer will be graded as REJECT, REPOLISH, or RECLEAN and in the second instance the wafer will be graded as ACCEPTED.

Besides sorting the wafer to its proper cassette, the system has the capability for visually displaying the occurrence of flaws on each inspected wafer as well as printing a map or a histogram of each wafer in order that diagnostic information may be derived to correct the causes of any flaws that are attributable to the processing, prior to the inspection.

It is an object of the present invention to provide a reflective surface inspection system that detects the presence of the flaws on the surface and classifies each detected flaw according to its type.

It is another object of the present invention to provide an automatic inspection system for detecting the presence of several types of flaws on the surface of a material and to provide a grading of the surface based upon the number and type of detected flaws.

It is a further object of the present invention to provide an automatic reflective surface inspection system which automatically sorts the inspected surfaces according to their grade classification.

It is still another object of the present invention to provide a silicon wafer inspection system which can detect flaws down to the one micron size and determine whether the inspected wafer should be accepted, recleaned, repolished or rejected.

BRIEF DESCTIPTION OF THE DRAWINGS

FIG. 2 is an overall block diagram of the system of the present invention.

DETAILED DESCRIPTION OF THE PREFERRED EMBODIMENT

Figure 1:
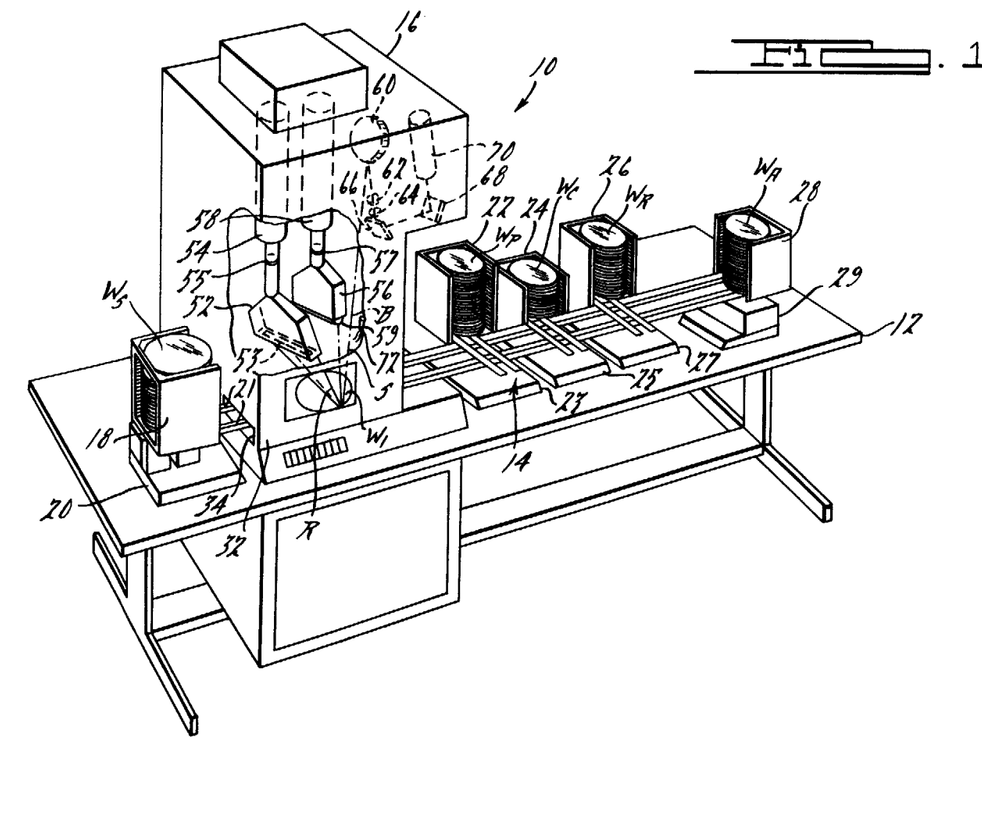
FIG. 1 is a plan view of the subject invention in a preferred configuration.

The embodiment of the inspection system invention 10, shown in FIG. 1, includes a support platform 12 for mounting a transport handling-system 14 and an optical inspection section 16.

The supply of reflective surface wafers $W_s$, to be inspected, are stored in a conventional supply cassette 18 that holds up to 25 individually separated wafers. The casette 18 is set on a supply elevator module 20 that is commercially available and is an industrial standard item. The elevator module 20 indexes the cassette in a vertical direction so as to sequentially place each wafer onto the transport spine 21. The transport spine 21 moves the supplied wafer $W_s$ toward the optical inspection section 16 at a constant speed of approximately 1.43 inches (3.50 cm) per second. The wafer $W_s$ enters the optical inspection section 16 through an aperture 34 defined in the inspection section housing 32. The wafer is then defined as an inspected wafer $W_i$.

Inside the housing 32, an optical scanning system provides a beam B that is focused to a 0.002-0.003 inch (50-75 microns) diameter spot at a defined inspection surface corresponding to the upper surface of the wafer $W_i$ transported through the inspection system. The beam is repeatedly scanned along the line on the inspection surface in a direction that is transverse to the wafer $W_i$ transport direction.

The beam B is derived from a low power HeNe laser generator 70. The beam emanating from the laser 70 is folded by front surface mirrors 68 and 66 and focused by lenses 64 and 62. The beam is directed to a multi-faceted rotating mirror scanner 60 having 18 facets and rotating at approximately 3600 rpm.

A scan start detector 72 is located to receive the scanning beam B prior to the beam reaching the inspection surface. The detector 72 responsively generates a SCAN START signal that is employed in the analysis of the information received during inspection of the wafer $W_i$. Two separate fiber optic collectors are employed to receive scanning beam light reflected from the upper surface of the wafer $W_i$. A reflection collector 52 is oriented above the inspection surface in such a way as to receive specularly reflected light along path R. The collector 52 contains a narrow slit aperture mask on its receiving surface so that any change in the parallelism of the wafer $W_i$, that causes the reflected beam R to move transverse with respect to the slit, will be detected. The light collected by the reflection collector 52 is passed through a dichroic filter 55 to eliminate any light other than that of the scanning beam wavelength (632 millimicrons). Light passed by the dichroic filter 55 is detected by a photo-multiplier tube 54. Since light of varying intensities is normally always present in the specularly reflected beam while it is on the surface of the wafer $W_i$, the collector 52 and the photomultiplier 54 are considered as defining a "light channel detector".

A scattered light collector 56 receives a portion of light along path S that is scattered by any light diffusing particle of surface perturbation. The collector 56 contains a light gathering element 59 on the receiving surface thereof and a dichroic filter 57, identical to filter 55. The scattered light passing through the dichroic filter 57 is detected by a photomultiplier tube 58. The collector 56 and photomultiplier 58 are considered as defining a "dark channel detector".

The electrical outputs of the photomultiplier tubes 54 and 58 are thresholded and processed to detect flaws by amplitude and frequency analysis. The circuitry for analyzing the inspection information is described hereinafter in more detail.

The results of the inspection analysis provides a sorting disposition instruction to the transport handling system 14 so that the inspected wafer $W_i$ will be routed into one of a plurality of cassettes 22, 24, 26 or 28.

The cassette 22 stores wafers designated as $W_p$, that are classified as needing to be repolished. The cassette 22 is set on an elevator module 23 and is indexed to receive the next appropriately inspected and graded wafer $W_p$.

The cassette 24 contains wafers designated as $W_c$, which are classified as needing to be recleaned. The cassette 24 is set on an elevator module 25 and is indexed to receive the next appropriately inspected and graded wafer $W_c$.

The cassette 26 contains wafers designated as $W_r$, which are classified as rejected. The cassette 26 is set on an elevator module 27 and is indexed to receive the next appropriately inspected and graded wafer $W_r$.

The cassette 28 is positioned to receive acceptable wafers designated as $W_a$. The cassette 28 is set on an elevator module 29 and is indexed to receive the next appropriately inspected and graded wafer $W_a$.

The electrical portion of the system is shown in block diagram format in FIG. 2 and is divided into respective transport, scanner, electronics and control panel sections.

The scanner section is conceptually identical to that shown in FIG. 1, wherein the inspected wafer $W_i$ is transported along a direction T and specularly reflected light is transmitted along the path R to the light channel photomultiplier detector tube 54. Any flaws present on the inspected $W_i$ that cause scanned light to be scattered along the path S are detected by the dark channel photomultiplier detector tube 58. The scan start detector 72 is also indicated and provides a SCAN START pulse prior to each line scan of the inspected wafer $W_i$. The light and dark channel detectors output corresponding signals on lines L and D respectively that are fed to an analog circuit 100, in the electronic section.

The analog section provides 7 channels of real time information in the form of a seven-bit address on threshold category channel lines $T_1, T_2, T_3, T_4, T_5, T_6$ and $T_7$. The flaw information in the seven-bit address channels is derived by comparing the electrical output signals from the light and dark channels with various threshold levels, in the case of the dark channel signals; and by extracting various frequency components and comparing those components with predetermined threshold levels in the case of the light channel signals.

The seven-bit address is applied to the digital flaw identification and processing network 200 where it is used to construct a digital (matrix) surface map of the wafer under inspection. In constructing the digital surface map, the scanned wafer is divided into a large number of minute unit areas and each unit area is assigned a binary code representing the most severe flaw type encountered within that unit area. A video monitor 400 and a map printer 402 may be employed to respectively visually display the occurrence of each flaw found in the inspected wafer and preserve that display information. The digital flaw and identification processing network 200 also serves the function of classifying and counting each type of flaw. It also provides for the grading of each inspected wafer according to predetermined standards as communicated thereto via the keyboard 408, which is interfaced through a peripheral interface adapter 302, an auxiliary computer 300 and an interface port 301. The grading information is output from the digital flaw identification and processing network 200 through the interface port 301 to the computer 300 which appropriately instructs the transport system to route the wafer to the corresponding cassette and index that cassette to its next position via its corresponding elevator module through the peripheral interface adaptor 302. The location of the wafer is tracked by wafer position sensors positioned along the path of transport.

A printer 404 and a character display 406 are also included in order to list each inspected wafer according to its sorted disposition, grade and number of each type of identified flaw.

Figure 3A:
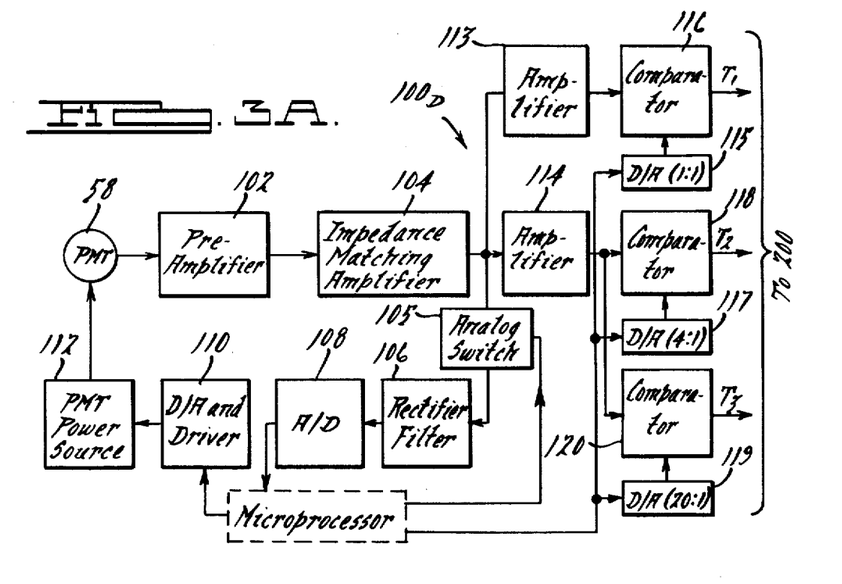
FIG. 3A is a block diagram of the dark channel analog portion of the system.

The dark channel analog circuit 100$_D$ is dedicated to processing the light variations resulting when surface imperfections cause an increase in scattered light. A block diagram is shown in FIG. 3A.

The processing for this channel utilizes signal conditioning amplifiers including preamplifier 102, impedance matching amplifier 104 and amplifiers 110 and 114. Threshold comparator circuits 116, 118 and 120 compare the amplified output of the dark channel detector with threshold levels having respective signal to noise ratios of approximately 1:1; 4:1; and 20:1 from corresponding digital to analog converters 115, 117 and 119.

The reference voltages for threshold levels are derived from a microprocessor where the individual digital threshold values $DT_1$-$DT_3$ are stored and applied to the analog comparators via the aforementioned digital to analog converters 115, 117 and 119. The threshold category channel output signals are designated $T_1$, $T_2$ and $T_3$.

A photomultiplier gain control circuit is used to provide long term stability of signal levels by compensating for degradation of the laser source intensity, photomultiplier tube and/or circuitry. The output of the photomultiplier tube 58 is sampled when the laser beam is off the wafer surface and is representative of the noise level reference at the comparator input. An analog switch 105 is gated by the microprocessor and samples a noise level signal which is then amplified and rectified by filter 106 to obtain a D.C. level representative of the noise amplitude. Four samples are made by an analog to digital converter and sent to the microprocessor where an average value is determined. This value is then averaged with four previously averaged values to define a new digitally coded value representing the system gain level. This level is converted to an analog voltage via a digital to analog converter 110. The analog voltage is applied to the PMT power source 112 which adjusts the high voltage (and effectively the gain of PMT 58) to maintain a constant background noise amplitude.

Figure 3B:
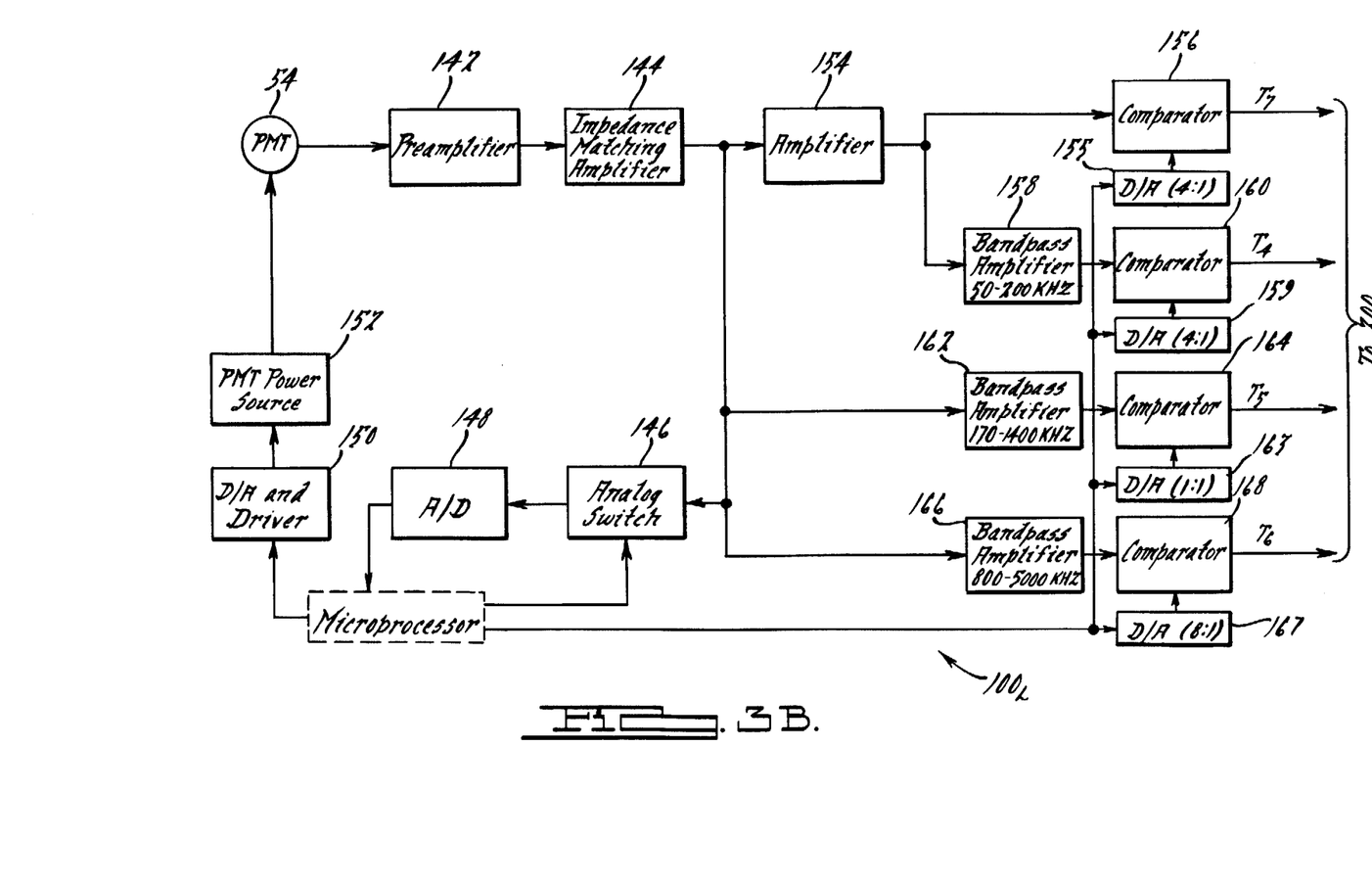
FIG. 3B is a block diagram of the light channel analog portion of the system.

The light channel analog circuit 100$_L$ is shown in FIG. 3B and is dedicated to processing the light variations resulting from imperfections on the surface of the inspected $W_i$ which cause a loss (change) in the received specular reflected light. The processing in the analog circuit shown in 3B for the light channel is quite similar to that shown in FIG. 3A in that the photomultiplier tube 54 provides an output signal to a preamplifier 142. The output of the preamplifier 142 is fed to an impedance matching amplifier 144 and that output is fed to an amplifier 154.

Automatic gain control of the PMT signal strength is performed in a manner as previously described with respect to the dark channel analog circuit 100$_D$, with one significant difference. Control of the signal strength is determined by sampling the light level when the laser beam is on the wafer, as opposed to the noise level control of the dark channel. The automatic gain control circuit provided in the light channel circuit 100$_L$ comprises an analog switch 146, which receives the output from the impedance matching amplifier 144 and a sampling gate signal from the microprocessor. The output of the analog gate 146 is fed to an analog to digital converter circuit 148. The output of the converter 148 is fed to the microprocessor where it is compared and averaged as described in the discussion of dark channel analog circuit 100$_D$. The digitally coded value representing the system gain level is converted to an analog voltage by a digital to analog converter 150. The analog voltage is applied to the PMT power source 152, which responsively adjusts the high voltage to maintain a normally constant signal amplitude level.

The output of the impedance matching amplifier 144 is fed to a band pass amplifier 162 which passes frequency components within the mid-range of 170–1400 KHz to a comparator circuit 164. A bandpass threshold level having a signal-to-noise ratio of approximately 1:1 is also input to the comparator 164 from a digital to analog converter 163, which is connected to receive a digital threshold value $DT_5$ from the microprocessor. The output state of the comparator 164 changes whenever the output of the bandpass amplifier 162 exceeds the 1:1 bandpass threshold level and outputs a signal correspondingly indicative of the state change on $T_5$.

The output of the impedance matching amplifier 144 is also fed to a bandpass amplifier 166 which passes frequency components in that signal falling within the high range of 800–5000 KHz. The output of the bandpass amplifier 166 is fed to a comparator 168 where it is compared with a bandpass threshold level having a signal-to-noise ratio of approximately 8:1, as set by $DT_6$. Whenever the output of the bandpass amplifier 166 exceeds the 8:1 bandpass threshold level, the comparator 168 changes state and reflects that change by outputting a level signal on $T_6$.

The output of the impedance matching amplifier 144 is also fed to amplifier 154 and the output of the amplifier 154 is fed to a bandpass amplifier 158 which passes frequency components in that signal falling within the low range of 50–200 KHz. The output of the bandpass amplifier 158 is fed to a comparator 160 where it is compared with a bandpass threshold level having a signal-to-noise ratio of approximately 4:1, as set by $DT_4$. Whenever the output of the bandpass amplifier 158 exceeds the 4:1 bandpass threshold level, the comparator 160 changes state and outputs a change in signal level on line $T_4$.

The output of amplifier 154 is also fed to comparator 156 where it is compared with an edge detection threshold level having a signal-to-noise ratio of approximately 4:1, as set by $DT_7$. Whenever the signal output from the amplifier 154 indicates a severe deviation in the received light amplitude, the comparator 156 changes states and responsively outputs a level signal on line $T_7$ indicating an edge detection on the wafer.

The following table shows a listing of detected flaws in order of priority. Each flaw type is briefly described and is identified by the address output on lines $T_1$-$T_6$ and $T_7$, as well as the correspondingly assigned hexidecimal code.

TABLE

| | PRIORITY OF DEFECT TYPES | | |
|---|---|---|---|
| HEX NO. | PRIOR- ITY | THRESHOLD | TYPE |
| G | 1 | $T_7$ ($T_1$-$T_6$ disregard) | Edge and localized defects > 50 microns (1000000) |
| F | 2 | $T_6$, $T_4$ and $T_3$ ($T_1$ and $T_2$ disregard) | Undetermined distortion/abrasion (101100) |
| E | 3 | $T_6$ and $T_4$ ($T_1$ and $T_2$ disregard) | Undetermined distortion (101000) |
| D | 4 | $T_6$, $T_5$ and $T_3$ ($T_1$ and $T_2$ disregard) | Dust > 50 microns (110100) |
| C | 5 | $T_5$, $T_4$ and $T_3$ ($T_1$, $T_2$ & $T_6$ disregard) | Severe distortion with abrasions (011100) |

TABLE-continued
PRIORITY OF DEFECT TYPES

| HEX NO. | PRIORITY | THRESHOLD | TYPE |
|---|---|---|---|
| B | 6 | $T_5$ and $T_4$ ($T_1$, $T_2$ & $T_6$ disregard) | Saw Marks, Polished (011000) |
| A | 7 | $T_5$ and $T_3$ ($T_1$ & $T_2$ disregard) | Localized distortion defects with abrasion (010100) |
| 9 | 8 | $T_5$ ($T_1$, $T_2$, & $T_6$ disregard) | Distortion defects, high frequency, such as crators or dimples (010000) |
| 8 | 9 | $T_4$ and $T_3$ ($T_1$ and $T_2$ disregard) | Distortion with abrasion (001100) |
| 7 | 10 | $T_4$ ($T_1$ and $T_2$ disregard) | Distortion, low level, low frequency such as undulations or mounds (001000) |
| 6 | 11 | $T_3$ ($T_1$, $T_2$ and $T_6$ disregard) | Pits, abrasions > 20 microns (000100) |
| 5 | 12 | | Not used |
| 4 | 13 | $T_2$ ($T_1$ disregard) | Pits, scratches > 2 microns (000010) |
| 3 | 14 | $T_1$ and $T_6$ ($T_2$ disregard) | Dust (100001) |
| 2 | 15 | $T_1$ | Haze, scrubber scratches (000001) |
| 1 | 16 | $T_6$ | Noise (100000) |

Figure 5:
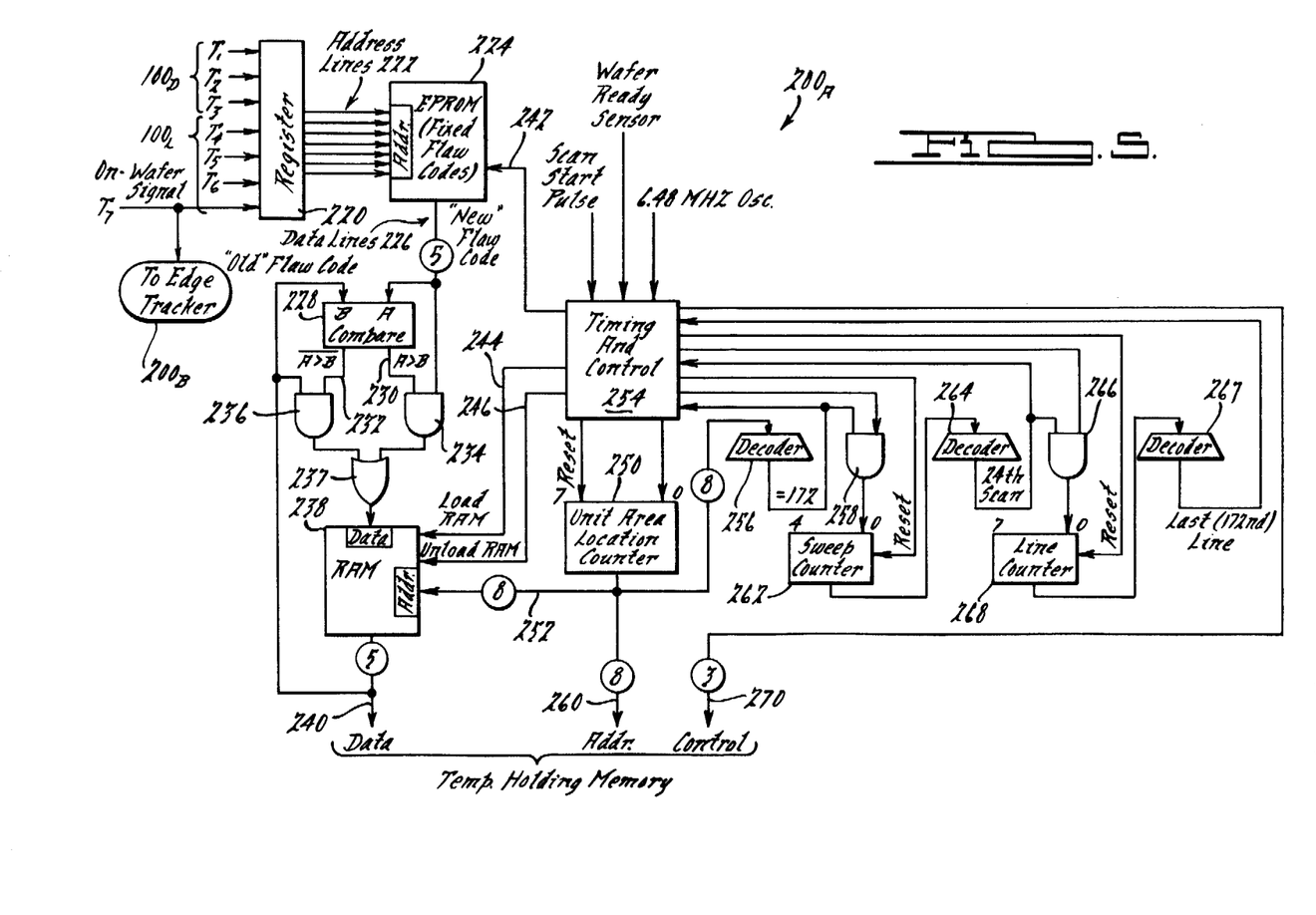
FIG. 5 is a block diagram of the edge tracker algorithm employed in the present invention.

The diagram of the digital flaw identification circuit 200A is shown in FIG. 5. The digital logic employed in the circuit 200A is used to construct a surface map of the wafer under inspection.

Figure 4:
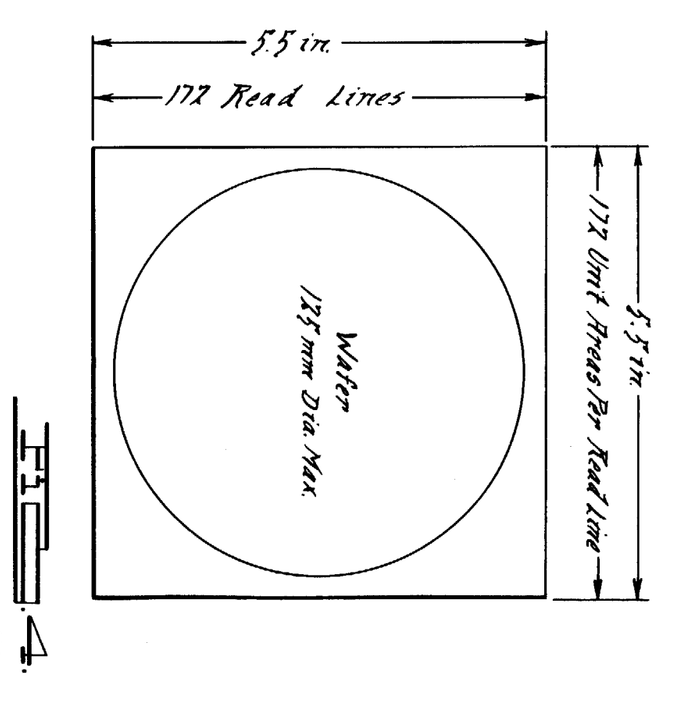
FIG. 4 is a conceptual view of the scan matrix of the system.

The matrix of the surface map, as shown in FIG. 4, has a dedicated 5.5×5.5 inch (13.9×13.97 cm) inspection area allowing the for the inspection of a wafer up to a maximum of 125 millimeter diameter. Since the wafer rests on a dark background, significant light receptive changes occur when the scan beam traverses a wafer edge. Accordingly, edge detection is made, based upon the signals appearing on $T_7$. Edge detection signals are used to gate sample the threshold signals $T_1$–$T_7$ only between the detected edges of the wafer. The unit area matrix shown in FIG. 4 consists of 172 read lines and 172 unit areas per read line (i.e., a matrix of 29,584 unit areas).

Referring again to FIG. 5, the digital flaw identification circuit 200A analyzes each scan line of information to provide the individual unit areas measuring 0.032×0.032 inch (0.813×0.813 mm) and each unit area will be designated with a binary code which represents the most severe flaw type encountered within that unit area. A unit area containing no flaws would be represented by an all zero's code. Construction of the surface map occurs on a sweep at a time basis and the digital flaw identification circuit 200A outputs a single read line of 172 unit areas to an associated microprocessor memory at the completion of every 24 sweeps of the scan beam.

Specifically, in FIG. 5, the three dark channel lines $T_1$, $T_2$ and $T_3$ from the analog portion 100$_D$ are gated to a latching register 220. Similarly, the four threshold channel lines $T_4$, $T_5$, $T_6$ and $T_7$ from the light channel analog circuit 100$_L$ are also gated to the latching register 220. $T_7$ from the light channel analog circuit 100$_L$ is also fed to an edge tracker circuit 200$_B$ which provides the gating of $T_1$–$T_7$ data between detected edges of the wafer $W_i$.

The register 220 is a temporary holding register which latches the seven bits of information on lines $T_1$–$T_7$ from the analog section and supplies a seven-bit address code for each of the 172 sampling unit areas for each scan of the beam. The contents of the register 220 are used as a seven-bit address for a 128×5 read-only memory (ROM) 224 which contains previously developed 5-bit codes in each of its 128 locations. Special cases are ROM location 0, which contains an all zero's code to indicate a condition of "no flaw"; and the upper 64 ROM locations, all of which contain the "on-wafer" code. ROM locations 1–63 contain codes appropriate to the specific combination of active thresholds relative to each sample location. The result is a five-bit code read out from the ROM 224 that defines the particular type of flaw represented by the correspondingly addressed location within the ROM 224. The five-bit code is defined such that the more severe the flaw, the greater numerical value of the code. The priority arrangement is illustrated in the table.

The five-bit code read out from the ROM 224 is referred to as a "new" flaw code and is compared with a corresponding, previously sampled five-bit code unloaded from a temporary holding RAM 238. The RAM 238 is synchronously addressed to unload the "old" flaw code stored in that address location corresponding to the same unit area along the scan beam that is currently being sampled and processed. A comparator 228 indicates when the "new" flaw code is greater than the "old" code and correspondingly provides an enabling signal on line 230 or 232 to an AND gate 234 or 236. The enabled AND gate 234 gates the "new" five-bit flaw code to load the RAM 238 and updates the "old" flaw code to indicate the most severe flaw detected in that unit area, when appropriate. Otherwise, the AND gate 236 is enabled to load the "old" flaw code back into RAM 238.

Since the speed of the wafer transport mechanism is such that the wafer moves 0.032 inches (0.813 mm) during the time required to process 24 scans, the sampling/comparison process is designed to occur 24 times for each unit area or 4,128 times for each of the 172 read lines that define the matrix of unit areas. A timing and control network 254 is employed to command and gate appropriate SCAN START; WAFER READY; and 6.48 MHz CLOCK signals to the appropriate logic units.

The RAM 238 is addressed 172 times per scan and that address is derived from a unit area location counter 250 which receives clocking signals gated through the timing and control network 254. Staggered UNLOAD and LOAD command signals are provided from the timing and control network 254 on lines 246 and 244 respectively. Upon the occurrence of the 172nd address for each scan line, a decoder 256, which monitors the eight-bit output of counter 250, provides an output that enables an AND gate 258. The enabled AND gate 258 passes a clock pulse to a sweep counter 262, which thereby monitors the number of sweeps of the scan beam. The output of the decoder 256 also provides a RESET signal to the unit area location counter 250. On the occurrence of the beginning of the 24th scan of the beam, the counter 262 feeds a decoder 264 that provides an output signal for enabling an AND gate 266. The enabled gate 266 passes a clock pulse to line counter 268, which thereby monitors the number of read lines fed to the temporary holding memory of the microprocessor. The output of the decoder 264 also provides a RESET signal to the sweep counter 262.

Upon the occurrence of the beginning of the 24th scan of the 172nd read line, a decoder 267 provides an output signal to the timing control network 254 that in turn provides a RESET signal to line counter 268.

The output of the decoder 264, provides a signal to the timing and control network 254 that acts not only to reset the sweep counter 262, but to also provide control data on three lines designated 270, in order to instruct the temporary holding memory of the associated microprocessor to read the next read line of 172 data and address words output on five data lines 240 and eight location address lines 260.

Upon the beginning of each 24th scan, a line of 172 unit area codes is transmitted to the microprocessor memory, for subsequent analysis, on lines 240. As each unit area code is transmitted, the appropriate location of the temporary holding RAM is cleared to an all zero's flaw code in preparation for processing the next read line. After 172 such read lines have been transmitted, the circuit $200_A$ suspends active processing and awaits the reception of the next wafer.

Wafer edge location coordinates are used by the microprocessor to determine the boundaries of the wafer within the overall 172×172 matrix. These coordinates are determined by the edge tracking logic $200_B$ shown in FIG. 6 and are employed to trigger a bistable flip flop that enables and disables AND gates to pass the $T_1$-$T_7$ signals from the analog circuit 100 to the digital flaw identification and processing circuit 200. In that manner, no extraneous signals from outside the wafer surface area will be processed as flaws that would otherwise show up in the accumulated flaw total.

Figure 6:
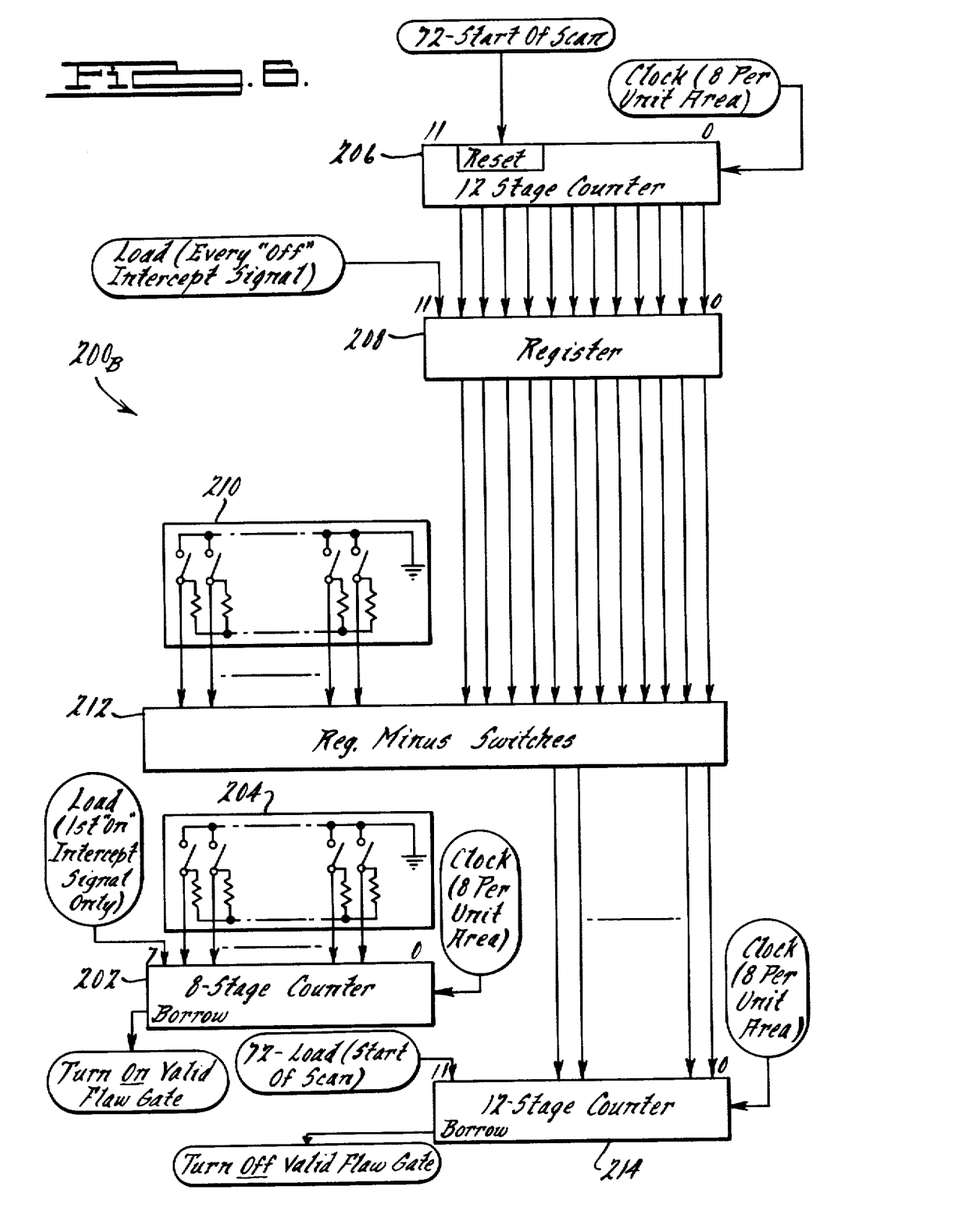
FIG. 6 is a block diagram of the flaw identification algorithm employed in the present invention.

The circuit $200_B$ illustrated in FIG. 6 is designed to record the first ON-wafer intercept and the last OFF-wafer intercept and to disregard all other signals which may appear as $T_7$ intercept. A latching arrangement prevents all but the first ON-wafer intercept signal from being recorded during the scan cycle. The OFF-wafer intercept portion of the circuit records the location along the scan at which the latch intercept occurs and uses that coordinate during the next scan in order that the occurrence of dirt or ash on the wafer will not be erroneously detected as an edge location of the wafer. DIP switches are implemented as part of the network for the purpose of providing locational adjustment of the perceived edges of the recreated ON-wafer signal. The adjustment defines an edge band on the wafer that is ignored for the purposes of flaw detection. The outer band on the wafer is not normally used for the production of integrated in semiconductor elements since, due to handling, the edges are most likely to contain an abundance of detectable flaws. These unwanted signals would otherwise result in false flaw information outside the limits of the wafer or along the wafer edge and thus produce an erroneous evaluation of the wafer.

The time period between the adjusted edges is referred to as the "valid flaw" time period and is provided to gate information from the analog circuit.

The edge tracker circuit $200_B$, shown in FIG. 6, employs an 8-stage down counter 202 which receives clocking pulses (8 per unit area) and is preloaded by DIP switches 204 connected to various stages of the counter 202. Upon receipt of the load instruction, corresponding to the $T_7$ transition indicating that the scan beam has traversed from a position of OFF-wafer to ON-wafer, the counter 202 begins to count clock pulses. When the counter 202 counts down from a total, which is equivalent to 2 or 3 unit areas as dictated by the preset setting of the DIP switches 204, the counter 202 produces a "borrow" output as an instruction to turn ON a valid flaw gate to allow passage of the signals on lines $T_1$-$T_7$.

In providing a turn OFF valid flaw signal, the circuit $200_B$ utilizes the previous line scan information determination of the last OFF-wafer intercept in determining the end of the valid flaw signal for the present scan.

A 12-stage counter 206 is reset to 0 upon receipt of the SCAN START signal from detector 72 and counts clock pulses (8 per unit area). The contents of the counter 206 are loaded into a register 208 each time an OFF-wafer intercept signal is received. The OFF-wafer intercept signal is a transition in the $T_7$ threshold line and, as explained earlier, false signals may be generated due to the presence of dust or ash.

An arithmetic logic unit 212 receives the information stored in the register 208 and subtracts a digital value preset by DIP switches 210 that define the marginal band at the edge of the wafer for which flaw detection is not desired.

Each time the OFF-wafer intercept signal is received, the register 208 is loaded with a new number from the counter 206 and provides that number to the arithmetic unit 12. The value is preloaded into a 12-stage down counter 214 upon receipt of the SCAN START signal for the next scan line from detector 72. When the counter 214 counts down to 0, from the preloaded value, a turn OFF valid flaw signal is output to inhibit receipt of information from the analog circuit on lines $T_1$-$T_7$.

The processing portion of the digital flaw identification and processing section 200, as shown in FIG. 2, comprises a microprocessor which is programmed to provide many of the output signals discussed above, and is also employed to analyze the 172 read lines of information output into its temporary holding memory. The flow diagram, illustrated in FIGS. 7A and 7B, illustrates the grading algorithm programmed into the microprocessor to provide the sort commands to the transport section and dictate the disposition of each inspected wafer.

Figure 7A:
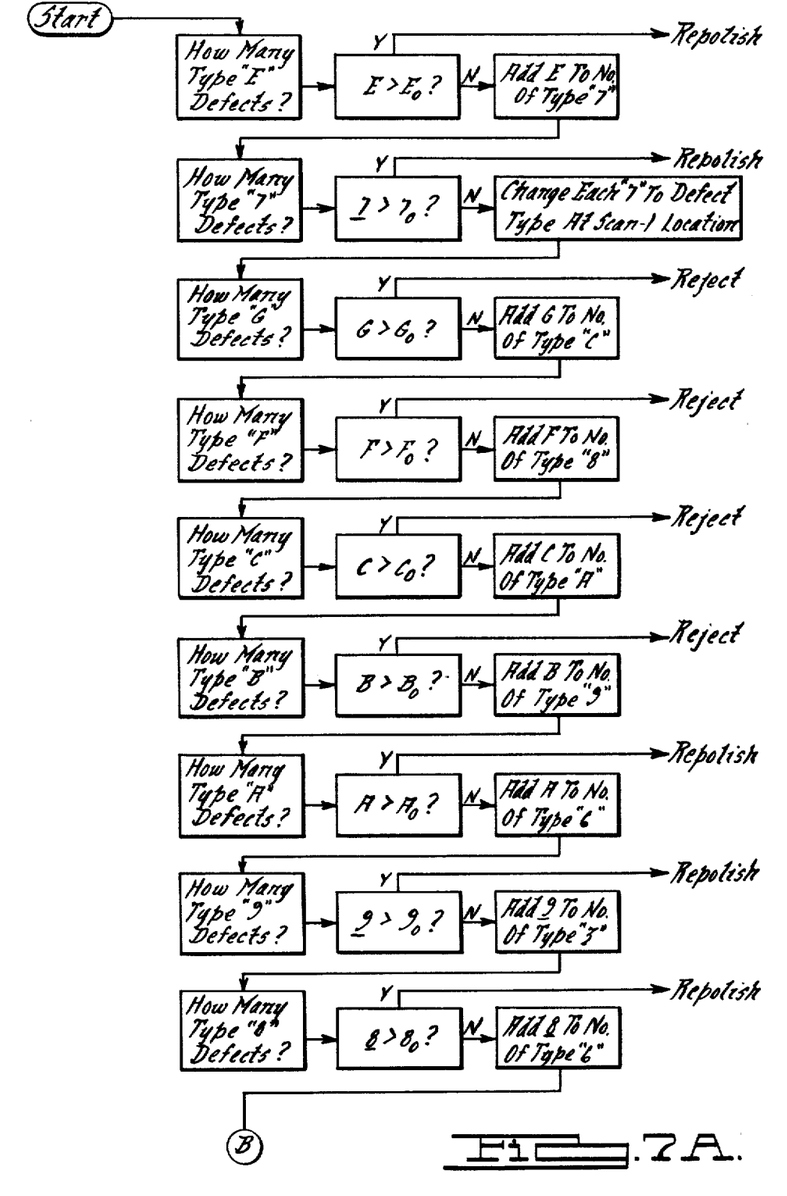
FIGS. 7A and 7B together illustrate a block diagram of the grading processing algorithm employed in the present invention.
Figure 7B:
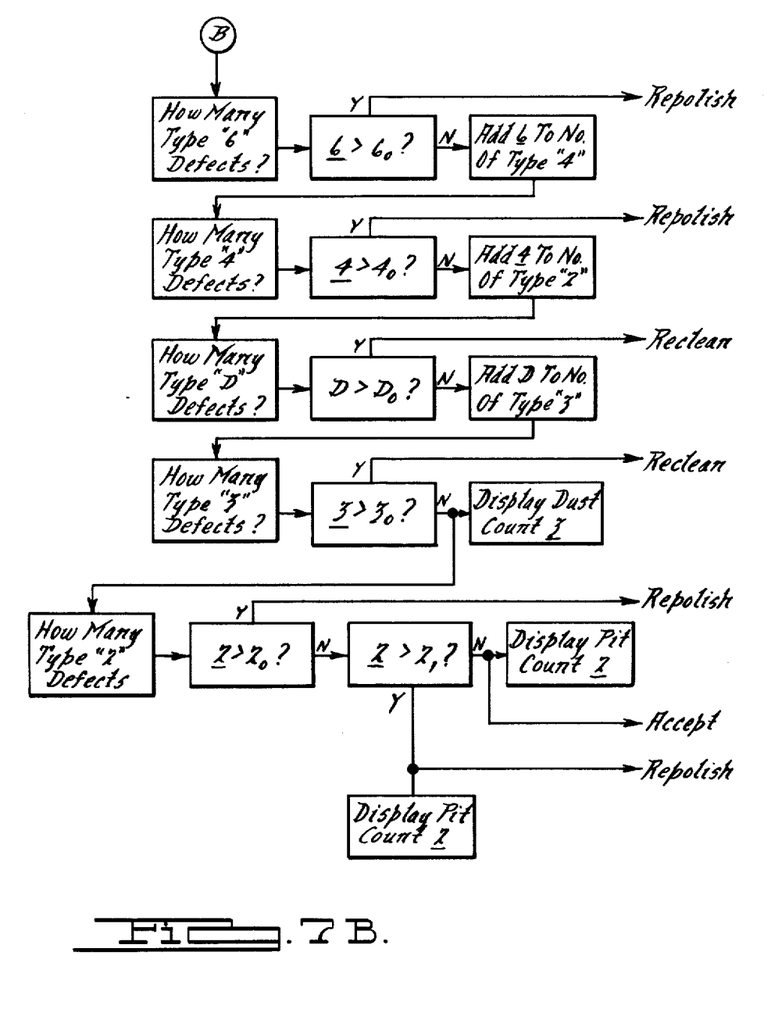

Referring to FIG. 7A, a START command is given and inquiry is made as to how many type "E" defects have been detected and are stored in the temporary holding memory. A maximum number of acceptable type "E" defects is preset into the system by the user and is designated as $E_0$. If the number E, of type "E" defects, is greater than $E_0$, the instruction is given to grade that wafer as REPOLISH. If the number E is not greater than $E_0$, the number E is added to the number of type "7" defects which have a lesser priority than the type "E" defects. Inquiry is then made into the number of type "7" defects which includes the number E. The number 7 of type "7" defects is compared with the preset maximum number designated as $7_0$ and they are compared. If the number 7 is greater than $7_0$, instruction is given to grade that wafer as REPOLISH. If 7 is less than or equal to $7_0$, each of the identified type "7" defects is redesignated as that type located in the immediately prior location.

It should be recalled that a type "7" defect, as shown in the Table, reflects a low frequency distortion and is sometimes found to also occur when previous location defects are detected. A low frequency ringing occurs, which sometimes results in a type "7" defect as being detected subsequent to the detection of another type. Therefore, when a low number of such type "7" defects are detected, they are reclassified as that type of defect which was detected in the next previous location, if any.

Following the reassignment of the type "7" defects, inquiry is made as to the number of type "G" defects. When that number G is greater than the preset maximum number $G_0$, the command is given to grade that inspected wafer as a REJECT.

The following instructions in the flow diagram, shown in FIGS. 7A and 7B, follow the general priority listing, as shown in the Table, until the lower priority defects are examined. In the case of the type "3" defects, when it is found that the number 3 of type "3" defects is greater than the preset maximum $3_0$, the instruction is given to grade the wafer as RECLEAN is not greater than the preset maximum number $3_0$, a DISPLAY DUST COUNT instruction is given to display the 3 number on the character display 406. Simultaneously, an inquiry is made as to the number of type "2" defects. The number 2 of type "2" defects is compared with the preset maximum number $2_0$ to determine whether the occurrence of type "2" defects indicates the presence of "haze" on the surface of the wafer. If 2 is greater than $2_0$, the instruction is given to grade the wafer as REPOLISH. If 2 is not greater than $2_0$, the number 2 is compared with a another preset maximum number $2_1$ that reflects the maximum number of "pits" that may be present on the surface. If the number 2 is greater than $2_1$, the pit count number 2 is instructed to be displayed on character display 406 and an instruction is given to grade the wafer as REPOLISH. If, on the other hand, 2 is not greater than $2_1$, an instruction is given to grade the wafer as ACCEPT and display the pit count number 2, if any.

Of course, upon the issuance of any of the instructional decisions such as ACCEPT, RECLEAN, REPOLISH or REJECT, the temporary memory is cleared and the system is reset to await the arrival of the next wafer at the inspection zone.

It will be apparent that many modifications and variations may be effected without departing from the scope of the novel concept of this invention, therefore, it is intended by the appended claims to cover all such modifications and variations which fall within the true spirit and scope of the invention.

We claim:

1. A flaw inspection system comprising:
   means defining an inspection surface;
   means for repeatedly scanning a narrow beam of electromagnetic radiation along a line across said defined inspection surface;
   means for transporting a reflective surface element to be inspected at a predetermined speed along said inspection surface in a direction transverse to said scanning line;
   means defining a normally light channel for receiving electromagnetic radiation specularly reflected from said transported element and producing a light channel output signal indicative of a change in said received specularly reflected radiation caused by flaws which may be present on said reflection surface;
   means defining a normally dark channel for receiving scattered electromagnetic radiation reflected from flaws which may be present on said reflection surface of said transported element and producing a dark channel output signal indicative of said scattered radiation received therein;
   first means connected to said light channel receiving means for comparing said light channel output signal with a first predetermined threshold level and outputting a predetermined signal level in a corresponding first threshold category channel whenever said light channel output signal and said first predetermined threshold level differ by a predetermined amount;
   second means connected to said light channel receiving means for passing portions of said light channel output signal having frequency components within a predetermined range of frequencies and for comparing said passed portions with a bandpass threshold level and outputting a predetermined signal level in a corresponding second threshold category channel whenever said passed portions of said light channel output signal and said bandpass threshold level differ by predetermined amounts;
   third means connected to said dark channel receiving means for comparing said dark channel output signal with a plurality of predetermined threshold levels and outputting a corresponding predetermined signal level in a corresponding threshold category channel whenever said dark channel output signal and a corresponding threshold level differ by predetermined amounts;
   means for time sampling said threshold category channels a plurality of times during each scan and over a plurality of successive scans to define a plurality of sampling areas;
   means for translating the occurrence of said output signal levels in said sampled threshold category channels into digital values according to the respective threshold category channels in which said output signal levels occurred;
   means for storing each digital value according to its time location in the scan;
   means for comparing said stored digital value with each successive digital value in a like time location within a corresponding sampling area and providing the greater of the compared digital values as the value designating the corresponding sampling area;
   means for accumulating the occurrences of like designated sampling areas; and
   means for evaluating the quality of said transported element according to preset accumulation values.

2. An inspection system as in claim 1, wherein said reflective surface element to be inspected is a silicon wafer and said scanning means includes a source of monochromatic radiation.

3. An inspection system as in claims 1 or 2, wherein said scanning means includes a laser generator for producing said narrow beam of electromagnetic radiation.

4. An inspection system as in claim 3, wherein said second comparing means includes a plurality of bandpass filters connected in parallel to receive said light channel output signal wherein each filter passes portions of said signal which has frequency components within a separate band of frequencies and the output of each filter is compared with a corresponding bandpass threshold level.

5. An inspection system as in claim 3, wherein said third comparing means includes three comparator circuits which receive respective threshold levels having signal to noise ratios of approximately 1:1, 4:1 and 20:1.

6. An inspection system as in claim 4, wherein said third comparing means includes three comparator circuits which receive respective threshold levels having signal to noise ratios of approximately 1:1, 4:1 and 20:1.

7. An inspection system as in claim 4, wherein said second comparing means includes a first bandpass filter that passes signals having frequency components within a band of frequencies from 50 to 200 KHz.

8. An inspection system as in claim 7, wherein said second comparing means includes a second bandpass filter that passes signals having frequency components within a band of frequencies from 170 to 1400 KHz.

9. An inspection system as in claim 8, wherein said second comparing means includes a third bandpass filter that passes signals having frequency components within a band of frequencies from 800 to 5000 KHz.

10. An inspection system as in claim 3, wherein said first, second and third means combine together to output a multi-bit address in their respective threshold category channels and said translating means includes a preprogrammed memory which contains flaw codes digitaly representing each flaw type according to a predetermined priority value and wherein said multi-bit address is applied to said memory; and said time sampling means provides a train of command signals to said memory.

11. An inspection system as in claim 10, further including means for detecting the commencement of each scan before said radiation reaches said defined inspection surface and outputting a scan start signal upon such detection;

said first means threshold level is set to only provide said predetermined signal level in said first threshold category channel when said amount of difference is approximately equal to the expected change between light reception from the inspection surface and light received from the reflective surface element;

means connected to receive said scan start signal and the output of said first means on said first threshold category channel for determining that portion of each scan for which received radiation contains information from the actual surface of the reflective surface element.

12. A method of inspecting a silicon wafer comprising the steps of:

providing an inspection surface;

repeatedly scanning a narrow beam of electromagnetic radiation along a line across said defined inspection surface;

transporting a reflective surface silicon wafer element to be inspected at a predetermined speed along said inspection surface in a direction transverse to said scanning line;

providing a normally light channel receiver for receiving electromagnetic radiation specularly reflected from said transported element and producing a light channel output signal indicative of any change in said received specularly reflected radiation caused by flaws which may be present on said reflection surface;

providing a normally dark channel receiver for receiving scattered electromagnetic radiation reflected from flaws which may be present on said reflection surface of said transported element and producing a dark channel output signal indicative of said scattered radiation received therein;

comparing said light channel output signal with a first predetermined threshold level and outputting a predetermined signal level in a corresponding first threshold category channel whenever said light channel output signal and said first predetermined threshold level differ by a predetermined amount;

passing portions of said light channel output signal having frequency components within a predetermined range of frequencies and comparing said passed portions with a bandpass threshold level and outputting a predetermined signal level in a corresponding second threshold category channel whenever said passed portions of said light channel output signal and said bandpass threshold level differ by predetermined amounts;

comparing said dark channel output signal with a plurality of predetermined threshold levels and outputting a corresponding predetermined signal level in a corresponding threshold category channel whenever said dark channel output signal and a corresponding threshold level differ by predetermined amounts;

time sampling said threshold category channels a plurality of times during each scan and over a plurality of successive scans to define a plurality of unit sampling areas;

translating the occurrence of said output signal levels in said sampled threshold category channels into digital values according to the respective threshold category channels in which said output signal levels occurred;

storing each digital value according to its time location in the scan;

comparing said stored digital value with each successive digital value in a like time location within a corresponding sampling area and providing the greater of the compared digital values as the value designating the corresponding sampling area;

accumulating the occurrences of like designated sampling areas; and evaluating the quality of said surface of said transported silicon wafer element according to preset accumulation values.

13. A method, as in claim 12, wherein said said step of scanning is performed by utilizing a source of monochromatic radiation.

14. A method as in claims 12 or 13, wherein said source is a laser generator for producing said narrow beam of electromagnetic radiation.

15. A method, as in claim 14, wherein said second step of comparing utilizes a plurality of bandpass filters connected in parallel to receive said light channel output signal, wherein each filter passes portions of said signal which has frequency components within a separate band of frequencies and the output of each filter is compared with a corresponding bandpass threshold level.

16. A method, as in claim 14, wherein said third step of comparing utilizes three comparator circuits which receive respective threshold levels having signal to noise ratios of approximately 1:1, 4:1 and 20:1.

17. A method, as in claim 15, wherein said third step of comparing utilizes three comparator circuits which receive respective threshold levels having signal to noise ratios of approximately 1:1, 4:1 and 20:1.

18. A method, as in claim 15, wherein said second step of comparing utilizes a first bandpass filter that passes signals having frequency components within a band of frequencies from 50 to 200 KHz.

19. A method, as in claim 18, wherein said second step of comparing utilizes a second bandpass filter that passes signals having frequency components within a band of frequencies from 170 to 1400 KHz.

20. A method, as in claim 19, wherein said second step of comparing utilizes a third bandpass filter that passes signals having frequency components within a band of frequencies from 800 to 5000 KHz.

21. A method, as in claim 14, wherein a multi-bit address is output on the collective threshold category channels and said step of translating utilizes a preprogrammed memory which contains flaw codes digitaly representing each flaw type according to a predetermined priority value and said multi-bit address is applied to said memory; and said time sampling step utilizes a train of command signals to said memory.

22. A method, as in claim 21, further includes the steps of detecting the commencement of each scan before said radiation reaches said provided inspection surface and responsively generating a scan start signal upon such detection;

said first predetermined threshold level is set to only provide said predetermined signal level in said first threshold category channel when said amount of difference is approximately equal to the expected change between light reception from the inspection surface and light received from the reflective surface element;

receiving both said scan start signal and the output on said first threshold category channel and determining that portion of each scan for which received radiation contains information from the actual surface of the reflective surface element.

* * * * *